United States Patent [19]
Diana

[11] 4,217,346
[45] Aug. 12, 1980

[54] ARYLALKYL AND ARYLOXYALKYL PHOSPHONATES AS ANTIVIRAL AGENTS

[75] Inventor: Guy D. Diana, Stephentown, N.Y.
[73] Assignee: Sterling Drug Inc., New York, N.Y.
[21] Appl. No.: 27,257
[22] Filed: Apr. 5, 1979

Related U.S. Application Data
[62] Division of Ser. No. 912,502, Jun. 5, 1978.

[51] Int. Cl.² .................. A61K 31/66; C07F 9/40
[52] U.S. Cl. ............................ 424/214; 260/403; 260/946
[58] Field of Search .............. 260/946, 968, 403; 424/214

[56] References Cited
U.S. PATENT DOCUMENTS

| | | | |
|---|---|---|---|
| 3,917,718 | 11/1975 | Collins | 568/644 |
| 4,031,246 | 6/1977 | Collins et al. | 424/331 |
| 4,045,468 | 8/1977 | Kurono et al. | 260/946 X |

OTHER PUBLICATIONS
Baron et al., "Annual Reports in Medicinal Chemistry", vol. 10 (1975), Chapter on Antiviral Agents, p. 166.
Linn et al., "J. Am. Chem. Soc.", vol. 87, (1965), pp. 3657–3672.

*Primary Examiner*—Anton H. Sutto
*Attorney, Agent, or Firm*—Thomas L. Johnson; B. Woodrow Wyatt

[57] ABSTRACT

Arylalkyl and aryloxyalkylphosphonates, useful as antiviral agents, are prepared by reacting an arylalkyl or aryloxyalkyl halide with a trialkyl phosphite, or with an alkali metal salt of a dialkyl phosphonate, trialkyl phosphonoalkanoate or dialkyl phosphonoalkanone.

13 Claims, No Drawings

ARYLALKYL AND ARYLOXYALKYL PHOSPHONATES AS ANTIVIRAL AGENTS

This application is a division of application Ser. No. 912,502, filed June 5, 1978.

BACKGROUND OF THE INVENTION

(a) Field of the Invention

The invention relates to arylalkyl- and aryloxyalkylphosphonates, to the preparation thereof, and to compositions and methods for the use thereof as antiviral agents.

(b) Description of the Prior Art

J. C. Collins U.S. Pat. No. 3,917,718, issued Nov. 4, 1975, discloses compounds useful as pesticidal and antiviral agents and having the formula

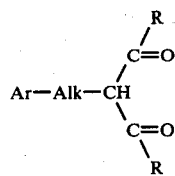

wherein Ar is phenyl or substituted phenyl, Alk is alkylene of 6–10 carbon atoms, and R is lower-alkyl. The compounds are prepared by reacting an arylalkyl halide, Ar—Alk—X, where X is bromine or iodine with an alkali metal salt of a diketone having the formula $H_2C(COR)_2$.

J. C. Collins and G. D. Diana U.S. Pat. No. 4,031,246, issued June 21, 1977, discloses compounds useful as pesticidal and antiviral agents and having the formula

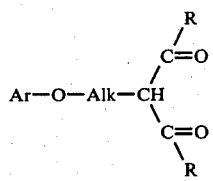

wherein Ar is phenyl or substituted phenyl, Alk is alkylene of 3–10 carbon atoms and R is lower-alkyl. The compounds are prepared by reacting an aryloxyalkyl halide, Ar—O—Alk—X, where X is bromine or iodine with an alkali metal salt of a diketone of the formula $H_2C(COR)_2$.

Sodium phosphonoacetate, $(HO)_2P(O)CH_2COONa$, has shown antiviral activity against herpes infections in test animals; cf. S Baron and G. Galasso, Chapter on Antiviral Agents, page 166, Annual Reports in Medicinal Chemistry, Vol. 10 (1975).

W. J. Linn and R. E. Bensen, J. Am. Chem. Soc. 87, 3657-72 (1965), at page 3671 disclose the compound diethyl (4-methylbenzyl)phosphonate, 4-$CH_3C_6H_4CH_2P(O)(OC_2H_5)_2$, as a chemical intermediate.

SUMMARY OF THE INVENTION

In a composition of matter aspect, the invention relates to compounds having the formula

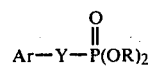   I wherein
Ar is phenyl or phenyl substituted by one or two substituents selected from the group consisting of halogen, lower-alkoxy of 1 to 4 carbon atoms, hydroxy, alkanoyloxy of 1–4 carbon atoms, carbolower-alkoxy of 2–4 carbon atoms, carbamyl and carboxy;
Y is $(CH_2)_n$ or $O(CH_2)_n$ wherein n is an integer from 6 to 8; and R is alkyl of 1–6 carbon atoms.

In a further composition of matter aspect, the invention relates to compounds having the formula

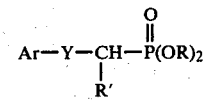   II wherein
Ar is phenyl or phenyl substituted by one or two substituents selected from the group consisting of halogen, lower-alkoxy of 1 to 4 carbon atoms, hydroxy, alkanoyloxy of 1–4 carbon atoms, carbolower-alkoxy of 2–4 carbon atoms, carbamyl and carboxy;
Y is $(CH_2)_m$ or $O(CH_2)_m$ where m is an integer from 3 to 10;
R is alkyl of 1–6 carbon atoms;
and
R' is alkanoyl or carboalkoxy of from 2 to 4 carbon atoms.

In a further composition of matter aspect, the invention relates to a composition for combatting viruses which comprises an antivirally effective amount of a compound of Formula I or II in admixture with a suitable carrier or diluent.

In a process aspect, the invention relates to a process for preparing a compound of Formula I which comprises heating a compound having the formula Ar—Y—X, where X is bromine or iodine, with a compound having the formula $P(OR)_3$ or an alkali metal salt of a compound having the formula $HP(O)(OR)_2$.

In a further process aspect, the invention relates to a process for preparing a compound of Formula II which comprises heating a compound having the formula Ar—Y—X, where X is bromine or iodine, with an alkali metal salt of a compound having the formula $R'CH_2$—$P(O)(OR)_2$.

In a further process aspect, the invention relates to a method of combatting viruses which comprises contacting the locus of said viruses with an antivirally effective amount of at least one compound of Formula I or II.

DETAILED DESCRIPTION INCLUSIVE OF PREFERRED EMBODIMENTS

The compounds of Formula I are prepared by either of two alternative methods, both starting from a common intermediate halide having the formula Ar—Y—X.

In the first method, the arylalkyl or aryloxyalkyl halide is heated with a trialkyl phosphite, $P(OR)_3$, preferably at a temperature between about 150° and 200° C. The relatively volatile alkyl halide, RX, is formed and distilled out of the reaction mixture leaving behind the product of Formula I which can be purified by distillation at reduced pressure or chromatographic procedures.

In the second method, the arylalkyl or aryloxyalkyl halide is heated with the alkali metal salt of a dialkyl phosphonate, HP(O)(OR)$_2$, said alkali metal salt being prepared in situ from the phosphonate and an alkali metal, preferably sodium or potassium, in an inert organic solvent prior to addition of the halide. The reaction occurs readily at a temperature between about 50° and 100° C., conveniently at the reflux temperature of the inert solvent, for example, hexane or tetrahydrofuran. In the event the arylalkyl halide or aryloxyalkyl halide is a bromide, the reaction can be catalyzed by the addition of a trace of iodine or sodium iodide.

The intermediate arylalkyl halides and aryloxyalkyl halides Ar—Y—X, are a known class of compounds, described in Collins U.S. Pat. No. 3,917,718 and Collins and Diana U.S. Pat. No. 4,031,246, respectively.

The compounds of Formula II are prepared by a process analogous to the second method for preparing the compounds of Formula I, that is, by reacting an arylalkyl halide or aryloxyalkyl halide, Ar—Y—X, with a compound having the formula R'CH$_2$P(O)(OR)$_2$ in the presence of a strong base, such as an alkali metal, e.g. lithium, sodium or potassium, or a strong base derived therefrom, e.g. a hydride or amide, which forms the alkali metal salt of the phosphonate involving the active methylene group (CH$_2$) intervening between the carbonyl function (R') and the phosphorus atom. The reaction takes place in an inert organic solvent at a temperature between room temperature and about 100° C.

The compounds of formulas I and II where Ar is substituted by carbamyl or carboxy are preferably prepared by reacting the corresponding compounds when Ar is substituted by carbo-lower-alkoxy with ammonia or with an alkaline hydrolysis medium, respectively; although it is possible to effect the functional group conversion prior to the phosphonate alkylation process if desired.

The structures of the compounds of the invention were established by the modes of synthesis, by elementary analysis, and by infrared and nuclear magnetic resonance spectral determinations.

Biological evaluation of the compounds of the invention has shown that they possess antiviral activity. They are thus useful in combatting viruses present on inanimate surfaces as well as viral infections in animal organisms. The in vitro testing of the compounds of the invention against herpes simplex viruses types 1 and 2 and various RNA viruses has showed that they inhibited viral growth at minimum concentrations (MIC) ranging from about 0.4 to about 25 micrograms per milliliter. The MIC values were determined by standard serial dilution procedures. In vivo activity has also been demonstrated in the treatment of mouse genital herpes simplex type 2 infection, and guinea pig herpetic skin infection.

The antiviral compositions are formulated by preparing a dilute solution or suspension in an organic or aqueous-organic medium, for example ethyl alcohol, acetone, dimethyl sulfoxide, and the like; and are applied to the locus to be disinfected by conventional means such as spraying, swabbing or immersing. Alternatively, the compounds can be formulated as ointments or creams by incorporating them in conventional ointment or cream bases, such as alkylpolyether alcohols, cetyl alcohol, stearyl alcohol and the like; as jellies by incorporating them in conventional jelly bases such as glycerin and tragacanth; or as aerosol sprays or foams. The antivirally effective component of the composition is present in a concentration of between about 0.7 parts per million and about 5 percent by weight, depending upon the chemical species used, the object to be treated and the type of formulation employed. For disinfection of inanimate surfaces with aqueous or aqueous-organic solutions, concentrations in the lower part of the range are effective. For topical application in medical or veterinary use in the form of ointment, cream, jelly or aerosol, concentrations in the upper part of the range are preferred.

The following examples will further illustrate the invention without the latter being limited thereby.

EXAMPLE 1

Ethyl 8-(2-chloro-4-methoxyphenoxy)-2-(diethoxyphosphinyl)-octanoate [II; Ar is 2-Cl-4-CH$_3$OC$_6$H$_3$, Y is O(CH$_2$)$_6$, R is C$_2$H$_5$, R' is C$_2$H$_5$OCO].

Potassium metal (623 mg) was added in small portions to a solution of 3.5 g of triethyl phosphonoacetate in 20 ml of xylene. The mixture was heated at reflux for one hour and then a solution of 5 g of 6-(2-chloro-4-methoxyphenoxy)hexyl bromide in 5 ml of xylene was added. The reaction mixture was refluxed for five hours, then cooled and filtered, and the filtrate concentrated in vacuo. The residue was distilled in vacuo to give 3.7 g of ethyl 8-(2-chloro-4-methoxyphenoxy)-2-(diethoxyphosphinyl)octanoate, b.p. 188°–192° C. (0.04 mm); MIC vs. herpes simplex type 2=3 mcg/ml.

Anal. Calcd. for C$_{21}$H$_{34}$ClO$_7$P: C, 54.25; H, 7.37; Cl, 7.63. Found: C, 54.12; H, 7.41; Cl, 7.77.

EXAMPLE 2

(a) Diethyl acetonylphosphonate [CH$_3$COCH$_2$PO(OC$_2$H$_5$)$_2$].

Iodoacetone (56.5 g, 0.31 mole) was added dropwise over a 20 minute period to 41.4 g (0.31 mole) of triethyl phosphite at 0° C. The mixture was allowed to warm to room temperature and held there for 90 minutes. The crude product was distilled in vacuo and the fraction boiling at 76°–86° C. (0.3–0.35 mm) was collected, giving 12.2 g of diethyl acetonylphosphonate.

(b) Diethyl [1-acetyl-5-(4-methoxyphenyl)pentyl]phosphonate [II; Ar is 4-CH$_3$OC$_6$H$_4$, Y is (CH$_2$)$_4$, R is C$_2$H$_5$, R' is CH$_3$CO].

Lithium hydride (0.71 g, 0.09 mole) was added to 90 ml of dry dimethylformamide (DMF) under a nitrogen atmosphere. The mixture was stirred for 10 minutes and there was then added 17.2 g (0.089 mole) of diethyl acetonylphosphonate. The resulting mixture was stirred one hour at 50° C., then cooled and a solution of 25.8 g (0.089 mole) of 4-(4-methoxyphenyl)butyl iodide in 80 ml of DMF was added. The reaction mixture was stirred for 2 days at 40° C., and then concentrated in vacuo at 70° C. The residue was chromatographed on Florisil and eluted with the solvent series hexane-ether-methanol. Ether-methanol 90:10 brought out 12.4 g of diethyl [1-acetyl-5-(4-methoxyphenyl)pentyl]-phosphonate as a yellow oil; MIC vs. herpes simplex type 2=25 mcg/ml. The IR spectrum was consistent with the assigned structure.

Anal. Calcd. for C$_{18}$H$_{29}$O$_5$P: C, 60.65; H, 8.20; P, 8.69. Found: C, 60.57; H, 8.23; P, 8.89.

EXAMPLE 3

Diethyl [1-acetyl-8-(2-chloro-4-methoxyphenoxy)octyl]phosphonate

[II; Ar is 2-Cl-4-CH$_3$OC$_6$H$_3$, Y is O(CH$_2$)$_7$, R is C$_2$H$_5$, R' is CH$_3$CO] was prepared from 0.57 g of lithium hydride, 13.9 g of diethyl acetonylphosphonate and 27.8 g of 7-(2-chloro-4-methoxyphenoxy)-heptyl iodide according to the procedure of Example 2(b). The product was chromatographed on Florisil and further purified by preparative thin layer chromatography (TLC) on silica gel to give 5.9 g of diethyl [1-acetyl-8-(2-chloro-4-methoxyphenoxy)-octyl]phosphonate as a yellow oil; MIC vs. herpes simplex type 2=6 mcg/ml. The NMR spectrum was consistent with the assigned structure.

Anal. Calcd. for C$_{21}$H$_{34}$ClO$_6$P: C, 56.18; H, 7.63; P, 6.58. Found: C, 56.06; H, 7.73; P, 6.72.

Example 4

Diethyl [1-acetyl-9-(2-chloro-4-methoxyphenoxy)nonyl]phosphonate

[II; Ar is 2-Cl-4-CH$_3$OC$_6$H$_3$, Y is O(CH$_2$)$_8$, R is C$_2$H$_5$, R' is CH$_3$CO] was prepared from 0.38 g of lithium hydride, 9.5 g of diethyl acetonylphosphonate and 19.4 g of 8-(2-chloro-4-methoxyphenoxy)octyl iodide according to the procedure of Example 2(b). The product was chromatographed on Florisil to give 5.67 g of diethyl [1-acetyl-9-(2-chloro-4-methoxyphenoxy)nonyl]phosphonate as a light yellow oil; MIC vs. herpes simplex type 2=12 mcg/ml. The NMR spectrum was consistent with the assigned structure.

Anal. Calcd. for C$_{22}$H$_{36}$ClO$_6$P: C, 57.07; H, 7.83; P, 6.69. Found: C, 57.37; H, 7.90; P, 6.81.

EXAMPLE 5

Diethyl [1-acetyl-6-(2-chloro-4-methoxyphenoxy)hexyl]phosphonate

[II; Ar is 2-Cl-4-CH$_3$OC$_6$H$_3$, Y is O(CH$_2$)$_5$, R is C$_2$H$_5$, R' is CH$_3$CO] was prepared from 0.71 g of lithium hydride, 17.2 g of diethyl acetonylphosphonate and 34 g of 5-(2-chloro-4-methoxyphenoxy)pentyl iodide according to the procedure of Example 2(b). The product was chromatographed on Florisil and further purified by preparative TLC on silica gel to give 6.3 g of diethyl [1-acetyl-6-(2-chloro-4-methoxyphenoxy)hexyl]phosphonate as a light yellow oil; MIC vs. herpes simplex type 2=6 mcg/ml. The IR spectrum was consistent with the assigned structure.

Anal. Calcd. for C$_{19}$H$_{30}$ClO$_6$P: C, 54.21; H, 7.18; P, 7.36 Found: C, 54.09; H, 7.15; P, 7.49.

EXAMPLE 6

Diethyl [1-acetyl-5-(2-chloro-4-methoxyphenoxy)pentyl]phosphonate

[II; Ar is 2-Cl-4-CH$_3$OC$_6$H$_3$, Y is O(CH$_2$)$_4$, R is C$_2$H$_5$, R' is CH$_3$CO] was prepared from 0.79 g of lithium hydride, 19.4 g of diethyl acetonylphosphonate and 34.0 g of 4-(2-chloro-4-methoxyphenoxy)butyl iodide according to the procedure of Example 2(b). The product was chromatographed on Florisil to give 6.45 g of diethyl [1-acetyl-5-(2-chloro-4-methoxyphenoxy)pentyl]phosphonate as a yellow oil; MIC vs. herpes simplex type 2=12 mcg/ml. The NMR spectrum was consistent with the assigned structure.

Anal. Calcd. for C$_{18}$H$_{28}$ClO$_6$P: C, 53.14; H, 6.93; Cl, 8.71 Found: C, 53.30; H, 6.98; Cl, 8.70.

EXAMPLE 7

Diethyl [1-acetyl-7-(2-chloro-4-methoxyphenoxy)heptyl]phosphonate

[II; Ar is 2-Cl-4-CH$_3$OC$_6$H$_3$, Y is O(CH$_2$)$_6$, R is C$_2$H$_5$, R' is CH$_3$CO] was prepared from 0.47 g of lithium hydride, 11.6 g of diethyl acetonylphosphonate and 22 g of 6-(2-chloro-4-methoxyphenoxy)hexyl iodide according to the procedure of Example 2(b). The product was chromatographed on Florisil and further purified by preparative TLC on silica gel to give 5.0 g of diethyl [1-acetyl-7-(2-chloro-4-methoxyphenoxy)heptyl]phosphonate as a yellow oil; MIC vs. herpes simplex type 2=6 mcg/ml. The IR and NMR spectra were consistent with the assigned structure.

Anal. Calcd. for C$_{20}$H$_{32}$ClO$_6$P: C, 55.23; H, 7.92. Found: C, 54.91; H, 7.30.

According to the procedures of Examples 1–7, it is contemplated that the following intermediates:
6-phenylhexyl iodide
6-(4-fluorophenyl)hexyl iodide
6-phenoxyhexyl bromide
6-(4-bromophenyl)hexyl iodide
6-(4-iodophenyl)hexyl iodide
6-(4-hydroxyphenyl)hexyl iodide
6-(4-acetoxyphenyl)hexyl iodide
6-(4-carbethoxyphenoxy)hexyl bromide can be caused to react with diethyl acetonylphosphonate to give, respectively:

Diethyl (1-acetyl-7-phenylheptyl)phosphonate [II; Ar is C$_6$H$_5$, Y is (CH$_2$)$_6$, R is C$_2$H$_5$, R' is CH$_3$CO]

Diethyl [1-acetyl-7-(4-fluorophenyl)heptyl]phosphonate [II; Ar is 4-FC$_6$H$_4$, Y is (CH$_2$)$_6$, R is C$_2$H$_5$, R' is CH$_3$CO]

Diethyl (1-actyl-7-phenoxyheptyl)phosphonate [II; Ar is C$_6$H$_5$, Y is O(CH$_2$)$_6$, R is C$_2$H$_5$, R' is CH$_3$CO]

Diethyl [1-acetyl-7-(4-bromophenyl)heptyl]phosphonate [II; Ar is 4-BrC$_6$H$_4$, Y is (CH$_2$)$_6$, R is C$_2$H$_5$, R' is CH$_3$CO]

Diethyl [1-acetyl-7-(4-iodophenyl)heptyl]phosphonate [II; Ar is 4-IC$_6$H$_4$, Y is (CH$_2$)$_6$, R is C$_2$H$_5$, R' is CH$_3$CO]

Diethyl [1-acetyl-7-(4-hydroxyphenyl)heptyl]phosphonate [II; Ar is 4-HOC$_6$H$_4$, Y is (CH$_2$)$_6$, R is C$_2$H$_5$, R' is CH$_3$CO]

Diethyl [1-acetyl-7-(4-acetoxyphenyl)heptyl]phosphonate [II; Ar is 4-CH$_3$COOC$_6$H$_4$, Y is (CH$_2$)$_6$, R is C$_2$H$_5$, R' is CH$_3$CO]

Diethyl [1-acetyl-7-(4-carbethoxyphenoxy)heptyl]phosphonate [II; Ar is 4-C$_2$H$_5$OOCC$_6$H$_4$, Y is O(CH$_2$)$_6$, R is C$_2$H$_5$, R' is CH$_3$CO].

The last named compound can be hydrolyzed with sodium hydroxide in ethanol to give diethyl [1-acetyl-7-(4-carboxyphenoxy)heptyl]phosphonate [II; Ar is 4-HOOCC$_6$H$_4$, Y is O(CH$_2$)$_6$, R is C$_2$H$_5$, R' is CH$_3$CO].

It is further contemplated that diethyl [1-acetyl-7-(4-carbethoxyphenoxy)heptyl]phosphonate can be reacted with ammonia in ethanol to give diethyl [1-acetyl-7-(4-carbamylphenoxy)heptyl]-phosphonate [II; Ar is 4-H$_2$NCOC$_6$H$_4$, Y is O(CH$_2$)$_6$, R is C$_2$H$_5$, R' is CH$_3$CO].

I claim:

1. A compound having the formula

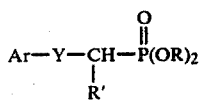

wherein
- Ar is phenyl or phenyl substituted by one or two substituents selected from the group consisting of halogen, lower-alkoxy of 1 to 4 carbon atoms, hydroxy, alkanoyloxy of 1–4 carbon atoms, carbo-lower-alkoxy of 2–4 carbon atoms, carbamyl and carboxy;
- Y is $(CH_2)_m$ or $O(CH_2)_m$ where m is an integer from 3 to 10;
- R is alkyl of 1–6 carbon atoms; and
- R' is alkanoyl or carboalkoxy of from 2 to 4 carbon atoms.

2. A method for combatting viruses which comprises contacting the locus of said viruses with an antivirally effective amount of at least one compound according to claim 1.

3. A compound according to claim 1 wherein Y is $O(CH_2)_m$.

4. A compound according to claim 1 wherein Ar is 2-chloro-4-methoxyphenyl and Y is $O(CH_2)_m$.

5. A compound according to claim 1 wherein Ar is 2-chloro-4-methoxyphenyl; Y is $O(CH_2)_m$ and R' is acetyl.

6. Ethyl 8-(2-chloro-4-methoxyphenoxy)-2-(diethoxyphosphinyl)octanoate, according to claim 4.

7. Diethyl [1-acetyl-5-(4-methoxyphenyl)pentyl]phosphonate, according to claim 1.

8. Diethyl [1-acetyl-8-(2-chloro-4-methoxyphenoxy)-octyl]phosphonate, according to claim 5.

9. Diethyl [1-acetyl-9-(2-chloro-4-methoxyphenoxy)-nonyl]phosphonate, according to claim 5.

10. Diethyl [1-acetyl-6-(2-chloro-4-methoxyphenoxy)-hexyl]phosphonate, according to claim 5.

11. Diethyl [1-acetyl-5-(2-chloro-4-methoxyphenoxy)-pentyl]phosphonate, according to claim 5.

12. Diethyl [1-acetyl-7-(2-chloro-4-methoxyphenoxy)-heptyl]phosphonate, according to claim 5.

13. A composition for combatting viruses which comprises an antivirally effective amount of at least one compound according to claim 1 in admixture with a suitable carrier or diluent.

* * * * *